United States Patent [19]

Bevan et al.

[11] 4,449,970
[45] May 22, 1984

[54] VENTING DEVICE FOR STOMA BAGS

[75] Inventors: David R. Bevan, Carshalton Beeches; Jeremy Layman, London, both of England

[73] Assignee: Downs Surgical Limited, Mitcham, England

[21] Appl. No.: 299,199

[22] Filed: Sep. 3, 1981

[30] Foreign Application Priority Data

Sep. 9, 1980 [GB] United Kingdom ............... 8029029

[51] Int. Cl.³ ............................................. A61M 1/00
[52] U.S. Cl. ................................. 604/333; 55/385 C
[58] Field of Search ............................. 604/332–345; 55/387, 385 C

[56] References Cited

U.S. PATENT DOCUMENTS 4,268,286  5/1981  Steer et al. .......................... 604/333

FOREIGN PATENT DOCUMENTS 2730286  1/1978  Fed. Rep. of Germany ...... 604/333

Primary Examiner—C. Fred Rosenbaum
Assistant Examiner—J. L. Kruter
Attorney, Agent, or Firm—Mason, Fenwick & Lawrence

[57] ABSTRACT

A flatus filter for attachment in a folded position over the edge of a stoma bag to cover opposed perforations in each of the two external walls of the stoma bag, comprising a gas-permeable pad containing an odor-absorbent substance affixed to one side of an elongate web, with at least a portion of the edges of the pad being exposed and/or with a portion of a major surface of the pad being exposed through one or more perforations in the said web adjacent to the pad, and with at least a portion of the side of the pad remote from the said web being exposed, or covered only by a removable protective backing sheet, and with that part of the filter surrounding the last-mentioned exposed portion being provided with an adhesive coating for attachment of the filter to a stoma bag.

12 Claims, 16 Drawing Figures

VENTING DEVICE FOR STOMA BAGS

BACKGROUND OF THE INVENTION

The present invention relates to a venting device (also known as a flatus filter) for attachment to a stoma bag, pouch or the like.

All people periodically expel gases (flatus) through the bowels, but such gas expulsion can cause problems for wearers of stoma bags, pouches or the like, such as colostomy bags, in that the gas tends to inflate the bag and, if there is sufficient build-up of gas within the bag, the bag can become detached from the wearer, with associated discomfort, risk of spillage, and the like. The problem can be overcome simply by periodically partially detaching the bag from the wearer, flattening it by hand to expel the gases, and then reattaching it. That solution can, however, be both tedious and embarrassing, as well as causing risk of leakage of liquid from the bag and possible skin irritation as a result of repeated detachment and attachment of the bag.

In order to overcome those problems, stoma bags have been provided with simple vent openings, which may be merely a small hole, such as a pin-hole, in the bag—and preferably toward the top of the bag to reduce risk of leakage. This is often sufficient to permit the emission of gases from the bag and thus avoid inflation of the bag.

The problem with a simple, continually open, vent, however, is that malodours may also be emitted, causing unpleasantness and embarrassment to the wearer. One way of overcoming that problem is to provide the bag with a controllable valve, which can be opened and closed as desired by the wearer, as described, for example, in U.S. Pat. No. 4,232,672 (which also contains a list of other patent specifications relating to various vented stoma appliances). It may, however, not always be convenient to open the valve in order to release the gases at the times when that proves necessary, and that can also cause embarrassment to the wearer. Moreover, such a valve is relatively complicated and increases the cost of the stoma appliance.

A second way of overcoming the problems associated with a simple, continually open, vent is to combine it with a deodourising means and/or with a filter to absorb the malodours. Various stoma appliances with in-built deodourising means and/or an in-built flatus filter have been described in, for example, U.S. Pat. No. 3,690,320, 3,865,109, GB Nos. 1,379,464 and 1,405,032.

Many commercially available stoma bags do not have such in-built deodourising means or flatus filters, however, and therefore various separate flatus filters are available for attachment to such bags. One such separate flatus filter available for attachment to a stoma bag is similar to an ordinary adhesive plaster but with a charcoal/felt pad in place of the normal absorbent pad of a plaster. It is essentially square, with a plastics backing sheet measuring about 4 cm×4 cm and adhesive on one side, and a charcoal/felt pad measuring about 2 cm×2 cm centrally situated on the adhesive side of the backing sheet covering a plurality of perforations in the backing sheet. In use, a pin-hole is made in one wall of the stoma bag toward the top and the filter is adhered to the wall of the bag with the charcoal/felt pad over the pin-hole. Gases are emitted from the bag through the pin-hole and then pass through the charcoal/felt pad, for absorption of malodours, before being discharged through the perforations in the backing sheet. A similar flatus filter, but with the charcoal/felt pad enveloped between a gas-permeable sheet, for attachment to the wall of the stoma bag, and a perforated gas-impermeable backing sheet is described in GB No. 1,462,492.

Another type of flatus filter consists of a charcoal/foam annular disc, adhesive on one face and with a circular plastics backing sheet covering the whole of the other face including the central hole. In use, this filter is also placed over a pin-hole in one wall of the bag with the central hole of the disc over the pin-hole. Gases emitted from the bag through the pin-hole, pass into the central hole of the flatus filter and then through the charcoal/foam pad, and out through its circumferential edge.

Yet another type of flatus filter is described in GB No. 1,550,960 and comprises a charcoal/foam or charcoal/felt pad coated on one side with a gas-permeable adhesive layer for attachment over a hole in a wall of a stoma bag, and coated on the other side with a gas-impermeable layer. Again, the gases are discharged through the circumferential edge of the filter.

We have discovered that a disadvantage of all those filters is that it is necessary to make a pin-hole in only one wall of the bag, which entails pulling the two walls of the bag apart and holding them apart while making the hole, which can be awkward. We have also found that sometimes the pin inadvertently pierces the other wall of the bag, or pierces the same wall of the bag in a second position, and this is not noticed, and that gases can then escape without passing through the filter, resulting in unpleasantness and possibly embarrassment to the wearer. Furthermore, the filters are not always adequately effective in absorbing malodours.

SUMMARY OF THE PRESENT INVENTION

The present invention provides a flatus filter for attachment in a folded position over the edge of a stoma bag to cover opposed perforations in each of the two external walls of the stoma bag, comprising at least one gas-permeable pad containing an odour-absorbing substance affixed to one side of an elongate web, with a portion of the or each pad being exposed to the atmosphere, and with at least a portion of the side of the or each pad remote from the said web being exposed, or covered only by a removable protective backing sheet, and with that part of the filter surrounding the last-mentioned exposed portion being provided with an adhesive coating for attachment of the filter to a stoma bag.

The portion of the or each pad exposed to the atmosphere may be a portion of the major surface of the or each pad adjacent to the web exposed through perforations in the web or exposed through a microporous web, or may be at least a portion of the edge of the pad.

In use, the flatus filter according to the invention is folded approximately in half substantially along its transverse axis and, after removing any protective backing sheet that nay be present, is affixed over the edge of a stoma bag so that the two halves of the filter adhere respectively to opposite walls of the bag and cover opposed perforations in the two walls. One of the perforations should be covered by the or a gas-permeable pad or an exposed portion of that pad and the other perforation may also be covered by the or another gas-permeable pad or an exposed portion thereof, or may simply be covered by the elongate web. In the former case, gases can be emitted through both of the perforations in the bag and thus through the filter, whereas in the latter case, gases can be emitted through only one of the perforations in the bag, the second perforation being sealed by the elongate web.

The flatus filter according to the invention has the advantage over the known flatus filter mentioned above that it is not necessary to perforate only one wall of the stoma bag prior to affixing the filter: both walls may be perforated simultaneously. Perforation of the walls may be effected simply by means of a pin or other pointed article or by means of a small hand punch, in which case the punch may include a stop to assist in effecting perforation at the optimum distance from the edge of the bag in relation to the dimensions of the filter. The size of perforations in the wall of the bag may be of the order of pin-hole size, that is to say about 0.2 to 0.5 mm, up to 1 to 2 mm.

A flatus filter according to the invention may have the further advantage of an improved effectiveness in absorbing malodours as compared with the known flatus filters mentioned above.

The flatus filter according to the invention is of elongate shape and may be, for example, of elongate rectangular shape or of elongate waisted shape. An elongate waisted shape, for example a dumbbell shape, is advantageous in that it tends to give a more compact shape along the edge of the bag when the filter is in position on the bag.

In a first type of flatus filter according to the invention, the gas-permeable pad is situated at or toward one end of the elongate web and positioned so as, in use, to cover the perforation in one wall of a stoma bag and the other end of the filter is adapted to seal the perforation in the other wall of the bag in a gas-tight manner.

In a second type of flatus filter according to the invention, a first gas-permeable pad is situated at or toward one end of the elongate web and is positioned so as, in use, to cover the perforation in one wall of a stoma bag, and a second gas-permeable pad is situated at or toward the other end of the elongate web and is positioned so as, in use, to cover the perforation in the other wall of the stoma bag.

In a third type of flatus filter according to the invention, the gas-permeable pad extends for the entire length or for a major part of the length of the elongate web and is positioned so as, in use, to cover the perforation in each wall of a stoma bag.

The first type of flatus filter as defined above has the advantage of being less bulky in use than the second and third types defined above. The second type is slightly less bulky than the third type and has the advantages over the first type of permitting a greater rate of gas emission and also of being effective for a longer period because of its greater volume of porous pad. The third type has the advantages over the other two types defined above of being effective for a still longer period and, especially when including some of the preferred features discussed below, of having a better effectiveness in absorbing malodours. It may also be easier to manufacture than the other two types of filter defined above.

In each of the three above-mentioned types of flatus filter according to the invention, the elongate web may extend beyond all edges of the gas-permeable pad, or the edges of the elongate web may coincide with the edges of the pad, over the whole of the filter in the case of the third type defined above or, in the case of the first and second types defined above, in the region or regions of the filter in which a pad or pads is or are situated.

In the case where the elongate web extends beyond all edges of the gas-permeable pad or pads, no edge portion of the pad will be exposed and it will be necessary for the elongate web to contain one or more perforations through which a portion or portions of the pad is or are exposed. On the other hand, in the case where the edges of the elongate web coincide with the edges of the pad over the whole or part of the filter, at least a portion of the edges of the pad or pads will normally be exposed and there will therefore be no need for the elongate web to contain perforations.

Each of the three above-mentioned types of flatus filter according to the invention advantageously additionally comprises a second web which at least substantially covers the side of the gas-permeable pad or pads remote from the first-mentioned web and which contains one or two perforations through which respectively one or two portions of the gas-permeable pad or pads is or are exposed, the said perforation or perforations in the said second web being positioned for alignment respectively with one or both of the opposed perforations in the two walls of the stoma bag.

In the case where the first-mentioned web extends beyond all edges of the gas-permeable pad or pads, the second web may be sealably joined to the first-mentioned web around all edges of the or each pad, such that the or each pad is encased between the first-mentioned web and the second web. The two webs may be of substantially the same size or one of the two webs may be larger than the other web. In the latter case, the one web may be larger than the other web overall and may extend beyond all edges of the smaller web, or one web may extend over only a part, for example a half, of the other web but, over that part, the edges of the two webs may coincide.

In the case where the edges of the first-mentioned web coincide with the edges of the pad over the whole or part of the filter, the edges of the second web advantageously also coincide with the edges of the pad over the whole or that part or those parts of the filter. In this case, the two webs will not normally be joined together in any place.

Advantageously, the side of the second web remote from the pad carries at least part of the adhesive coating. If the second web is of substantially the same size as the first-mentioned web, it is, of course, necessary for the second web to carry the whole of the adhesive coating. If, on the other hand, the first-mentioned web extends beyond all edges of the pad or pads and of the second web, the adhesive coating may be carried only on those parts of the first-mentioned web extending beyond the edges of the second web, but advantageously the second web also carries part of the adhesive coating. This ensures that there is, in use, good adhesion of the flatus filter to the bag and that consequently there is little risk of gases penetrating between the filter and the stoma bag and causing the filter to become lifted from the surface of the stom bag.

When the flatus filter according to the invention includes a second web and the first-mentioned web contains one or more perforations, it is preferred that the or each perforation in the first-mentioned web is displaced laterally with respect to the or each perforation in the second web. This ensures that gases cannot pass directly transversely through the gas-permeable pad but must take a lateral, and thus longer, path through the pad thus improving the effectiveness of the filter by increasing the degree of absorption of malodours by the pad. This may, for example, be achieved in one embodiment of the third type of flatus filter according to the invention as defined above in which a second web is present and contains two perforations positioned so as, in use, to cover respectively the perforation in each wall of the bag, by having one perforation in the first-mentioned web situated substantially equidistant from each of the two perforations in the said second web. Such positioning of the perforations in the two webs ensures that the gas takes the longest possible path through the pad and thus that the filter has a high degree of effectiveness.

When the first-mentioned web does not contain any perforations and at least a portion of the edges of the pad is exposed, the gases cannot pass transversely through the gas-permeable pad and must necessarily take a lateral pad through the pad in order to leave it through an edge.

In a flatus filter according to the invention, preferably substantially all surfaces of the gas-permeable pad adjacent to a web are adhesively secured to that web. This ensures that gases cannot pass around the pad instead of through it, thus by-passing the intended route for the gases.

The gas-permeable pad in a flatus filter according to the invention may be of any material that will permit the passage of gases therethrough and that can contain an odour-absorbent substance. It may, for example, be of a plastics foam material, another porous plastics material, felt, bonded fibres, or another textile material. The odour-absorbent substance may be impregnated into the gas-permeable material or may be encased in the gas-permeable material to give a pad in the form of a cushion. The odour-absorbent substance may be any substance known for absorbing odours from gases, for example chalk or, preferably, activated charcoal.

A flatus filter according to the invention may optionally include an odoriferous substance or a perfume to mask any malodours that may escape.

The web or webs in the flatus filter according to the invention may be of any suitable plastics or textile material, such as those materials conventionally used for adhesive plasters. The or each web is advantageously of a non-absorbent and non-porous material so that it does not permit the passage of gases therethrough and does not become wet should it accidentally come into contact with the contents of the stoma bag. Moreover, the or each web is advantageously of a non-allergenic material since parts of the filter may come into contact with the body of the wearer of the stoma bag. The or each web may, for example, suitably be of polyvinyl chloride or of a vinyl chloride copolymer.

The web may be formed integrally with the pad, for example by using a foam, felt or like material that is impregnated with an odour-absorbent substance in the region below one surface (constituting the pad) but not in the region below the opposed surface (constituting the web).

Prior to use of the filter according to the invention, the adhesive coating of the filter is suitably covered by a removable protective backing sheet. Such a protective backing sheet nay be of adhesive-repellent paper or of an adhesive-repellent plastics material, such as is conventionally used to protect adhesive coatings. The removable protective backing sheet may cover the perforation in the second web, and thus also cover the portion of the gas-permeable pad exposed through such perforation, or the backing sheet may contain one or more perforations aligned with said perforation in the second web.

Various forms of flatus filter according to the invention will now be described, by way of example only, with reference to the accompanying drawings.

BRIEF DESCRIPTION OF THE DRAWINGS

In the following description, and in the description of the preferred embodiments, the term "top" is used to refer to the side of the flatus filter that, in use, is remote from the stoma bag and other spacially relative terms are used accordingly.

In the drawings.

Figure 1:
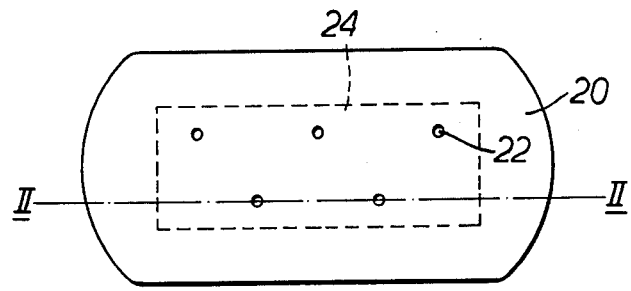
FIG. 1 shows a top plan view of one form of flatus filter according to the invention.

In all the cross-sectional views shown in the drawings the various layers of the flatus filter are, for clarity, shown spaced slightly apart, whereas, in practice, the various layers will, of course, be secured closely together.

DESCRIPTION OF THE PREFERRED EMBODIMENTS

Figure 2:
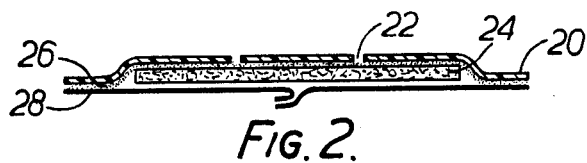
FIG. 2 shows a cross-section on the line II—II of FIG. 1.

The flatus filter shown in FIGS. 1 and 2 is substantially rectangular in shape but with rounded ends. In size, it may typically be of the order of 60 to 80 mm long by 20 to 40 mm. The filter includes an elongate plastics web 20 having a plurality of perforations 22, typically of the order of 0.3 to 2 mm in size. A charcoal-impregnated gas-permeable felt pad 24, typically measuring 50 to 60 mm by 10 to 20 mm with a thickness of 1 to 2 mm, is centrally situated on the underside of the elongate web 20 underlying all the perforations 22. The underside of the elongate web 20 is coated with an adhesive layer 26 by means of which the pad 24 is adhered to the elongate web 20 and by means of which the flatus filter may be secured to a stoma bag in the region of the elongate web 20 extending beyond the edges of the pad 24. A removable protective adhesive-repellent backing sheet 28, which is in two overlapping parts in order to aid its removal, covers the whole of the underside of the flatus filter prior to use.

Figure 3:
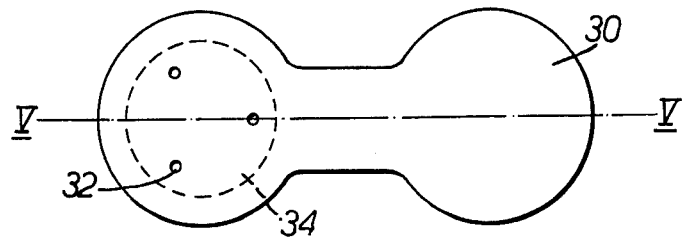
FIG. 3 shows a top plan view of another form of flatus filter according to the invention.
Figure 4:
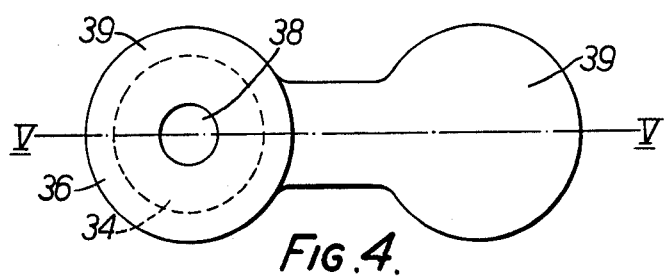
FIG. 4 shows an underneath plan view of the flatus filter shown in FIG. 3.
Figure 5:
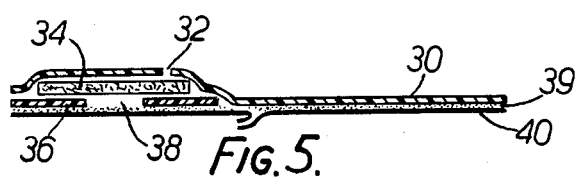
FIG. 5 shows a cross-section on the line V—V of FIGS. 3 and 4.

The flatus filter shown in FIGS. 3 to 5 is of dumbbell shape with its maximum length and maximum width typically being of the same order as the dimensions given for the flatus filter shown in FIGS. 1 and 2. The filter includes a dumbbell-shaped elongate web 30, one end of which contains three perforations 32 and to the same end of which is secured a circular charcoal-impregnated gas-permeable felt pad 34 underlying the three perforations 32. A circular second web 36, containing one central perforation 38, typically measuring 5 to 20 mm, is secured to the same end of the filter underneath the pad 34 in such a manner that the edge regions of the circular web 36 that extend beyond the edges of the pad 34 are adhered to the elongate web 30. The pad 34 is thus encased between one end of the elongate web 30 and the circular web 36. An adhesive layer 39 coats the entire underside of the filter, which, as may be seen in FIG. 5, comprises in part the circular web 36 and in part the elongate web 30 and, prior to use, is protected by a two-part removable protective adhesive-repellent backing sheet 40 (omitted from FIG. 4 for clarity).

Figure 6:
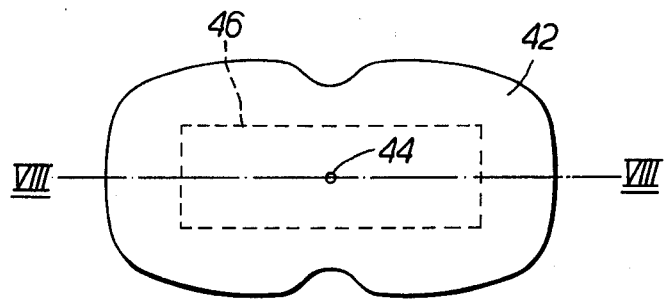
FIG. 6 shows a top plan view of a further form of flatus filter according to the invention.
Figure 7:
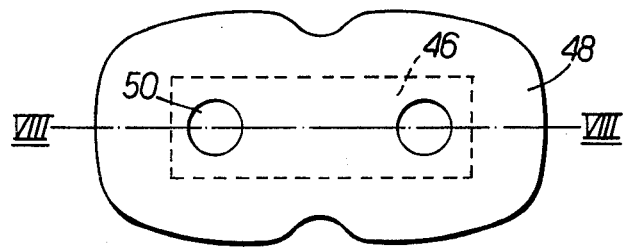
FIG. 7 shows an underneath plan view of the flatus filter shown in FIG. 6.
Figure 8:
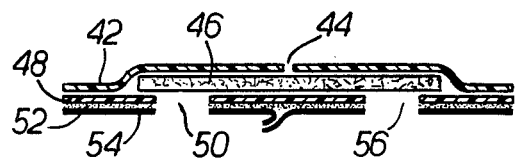
FIG. 8 shows a cross-section on the line VIII—VIII of FIGS. 6 and 7.

The flatus filter shown in FIGS. 6 to 8 is of elongate waisted shape and its maximum dimensions typically are of the same order as the dimensions given for the flatus filter shown in FIGS. 1 and 2. This filter includes an elongate web 42 containing a single central perforation 44 typically of the order of 0.2 to 2 mm with a rectangular charcoal-impregnated gas-permeable felt pad 46, typically of the same dimensions as the porous pad of the filter shown in FIGS. 1 and 2, centrally secured to the underside thereof. A second web 48 of identical external shape to the elongate web 42 underlies the pad 46 and the elongate web 42 and is adhered to the underside of the pad 46 and those parts of the elongate web 42 that extend beyond the edges of the pad 46. The pad 46 is thus encased between the elongate web 42 and the second web 48. The second web 48 contains two perforations 50, typically of the order of 5 to 20 mm, spaced equidistant from the perforation 44 in the elongate web 42. The entire underside of the second web 48 carries an adhesive coating 52 and, prior to use, this is protected by a two-part removable protective adhesive-repellent backing sheet 54 (omitted from FIG. 7 for clarity), which contains two perforations 56 corresponding to the perforations 50 in the second web 48.

Figure 9:
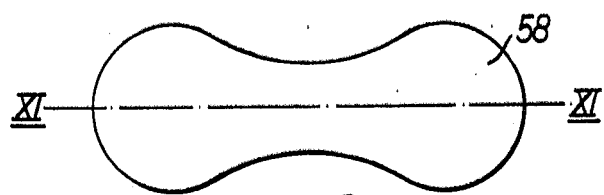
FIG. 9 shows a top plan view of a still further form of flatus filter according to the invention.
Figure 10:
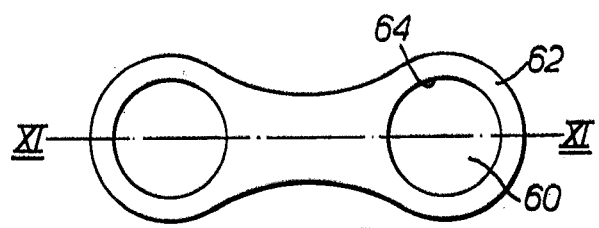
FIG. 10 shows an underneath plan view of the flatus filter shown in FIG. 9.
Figure 11:
FIG. 11 shows a cross-section on the line XI—XI of FIGS. 9 and 10.

The flatus filter shown in FIGS. 9 to 11 is of dumb-bell shape with its maximum length and maximum width typically being of the same order as the dimensions given for the flatus filter shown in FIGS. 1 and 2. The filter includes a dumb-bell-shaped elongate web 58 adhesively secured to one side of a charcoal-impregnated gas-permeable foam pad 60 which is of identical size and shape to the elongate web 58 and has a thickness typically of the order of 3 to 6 mm. A second web 62 of identical external shape to the elongate web 58 is adhesively secured to the underside of the pad 60, and this second web 62 is provided with two perforations 64 typically of the order of 5 to 20 mm diameter. The pad 60 is thus sandwiched between the elongate web 58 and the second web 62 with its edges exposed. The underside of the second web 62 carries an adhesive coating 66 and this in turn is covered by a two part removable protective backing sheet 68 (omitted from FIG. 10 for clarity), which contains two perforations 70 corresponding to the perforations 64 in the second web 62. This flatus filter is particularly easy to manufacture. A charcoal-impregnated foam sheet may be affixed to the sticky side of an adhesive-coated PVC sheet, for example, to form a PVC/foam laminate and articles of the desired shape may be cut from this sheet. A second PVC sheet, coated on both sides with adhesive and carrying a protective backing sheet on one side may also be cut and punched to form the second web 62 with its perforations 64, adhesive coating 66 and backing sheet 68. The exposed adhesive-coated side of the second web 62 may then be affixed to the exposed side of the foam pad 60.

Figure 12:
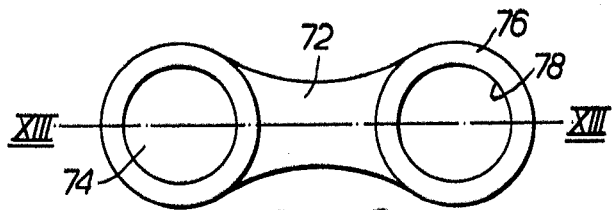
FIG. 12 shows an underneath plan view of yet another form of flatus filter according to the invention.
Figure 13:
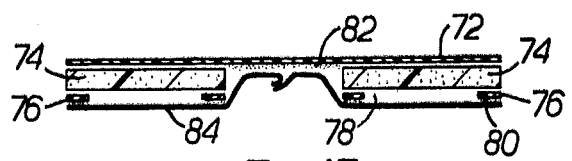
FIG. 13 shows a cross-section on the line XIII—XIII of FIG. 12.

The flatus filter shown in FIGS. 12 and 13 is also of dumb-bell shape and may be of similar dimensions to the flatus filter shown in FIGS. 9 to 11. The top plan view of this flatus filter corresponds to the top plan view of the previously described flatus filter as shown in FIG. 9. The filter includes a dumb-bell-shaped elongate web 72 to each end of which a circular charcoal-impregnated gas-permeable foam pad 74 is adhesively secured. A circular second web 76, having a perforation 78 and carrying on its underside an adhesive coating 80, is adhesively secured to the underside of each circular pad 74. The central region of the elongate web 72 between the two pads 74 also carries an exposed adhesive coating 82. A two-part removable protective backing sheet 84 (omitted from FIG. 12 for clarity) covers the entire underside of the flatus filter.

Figure 14:
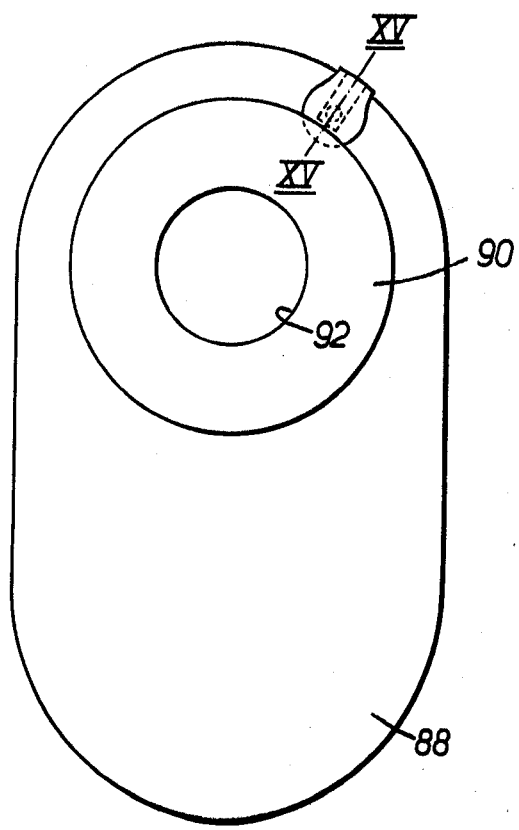
FIG. 14 shows a front view of a stoma bag to which a flatus filter as shown in FIGS. 6 to 8 is attached.
Figure 15:
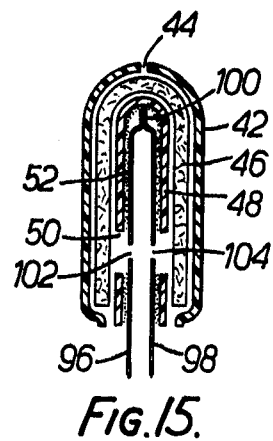
FIG. 15 shows a cross-section on the line XV—XV of FIG. 14.

A stoma bag 88, as shown in FIG. 14 and in part in FIG. 15 has an adhesive angular flange 90, by means of which it may be secured to the wearer, surrounding a circular opening 92, and essentially consists of two plastics sheet 96, 98 sealed together around their edges 100. Prior to affixing the flatus filter to the stoma bag, opposed perforations 102, 104, typically of the order of 0.2 to 2 mm, are made simultaneously through both walls 96, 98 of the bag a short distance in from the edge 100; these perforations may suitably be made by means of a small hand punch provided with a stop against which the edge 100 can abut in order to ensure that the perforations 102, 104 are made at the desired distance in from the edge 100. As shown in FIGS. 14 and 15, the flatus filter shown in FIGS. 6 to 8 has had its protective backing sheet 54 removed and has been affixed in a folded position reentrant over the peripheral edge of the bag such that the two perforations 50 in the second web 48 are aligned with the perforations 102, 104 in the walls 96, 98 of the bag. The single perforation 44 in the elongate web 42 then lies on the fold in the filter. In order to be emitted from the bag 88, gases must pass through the perforations 102, 104 in the walls 96, 98 of the bag, then through the perforations 50 in the elongate web 48, and then longitudinally through the pad 46 until they can leave through the perforation 44 in the elongate web 42. The porous pad 46 is adhered to the underside of the elongate web 42 and the top side of the second web 48, thus ensuring that the gases cannot by-pass this longitudinal path through the porous pad 46. This longitudinal path ensures that there is a high degree of absorption of malodours from the gases by the charcoal present in the pad 46.

Figure 16:
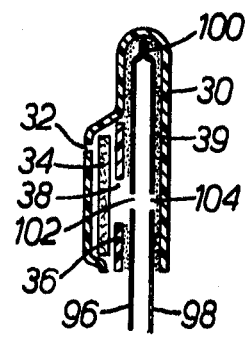
FIG. 16 shows a cross-section similar to that of FIG. 15 but with the filter shown in FIGS. 3 to 5 rather than shown in FIGS. 6 to 8.

In the embodiment shown in FIG. 16, perforations 102, 104 have been made in the walls 96, 98 of the stoma bag as described with reference to FIGS. 14 and 15. The dumbbell-shaped flatus filter shown in FIGS. 3 to 5 has been affixed in a folded position reentrant over the peripheral edge 100 of the bag in such a manner that the perforation 38 in the circular web 36 is aligned with the perforation 102 in the wall 96. The perforation 104 in the wall 98 is sealed by the elongate web 30 and the adhesive layer 39. In order to be emitted from the bag, gases must thus pass through the perforation 102, then through the perforation 38, and then a short longitudinal distance through the pad 34 until they can leave through the perforation 32 in the elongate web 30. The positioning of the perforations 32 in the elongate web 30 ensures that gases cannot pass directly transversely through the porous pad 34, and the pad 34 is adhered on its top side to the elongate web 30 and on its underside to the circular web 36 thus ensuring that the gases cannot by-pass this longitudinal path through the pad 34.

The various embodiments described above are only illustrative of the venting device according to the invention and various alterations and modifications may be made thereto, as will be apparent to those skilled in the art, without departing from the spirit of the invention or from the scope of the appended claims.

What is claimed is:

1. A venting device for attachment in a folded reentrant position over the peripheral edge of a stoma bag, said stoma bag having two opposed external walls with opposed perforations in said walls wherein the filter covers the opposed perforations in each of the two external walls of the stoma bag, the filter comprising
    a first elongated web,
    a second web,
    at least one gas-permeable pad containing an odourabsorbing substance and sandwiched between said webs, each pad having two major surfaces and an edge.
    at least a portion of that major surface of each pad adjacent said second web being arranged such that, in use, it is exposed to and aligned with at least one of said opposed perforations,
    a second portion of each pad being, in use, exposed to the atmosphere for venting of gas from the bag,
    the said second web containing at least one perforation through which such portions of each gas-permeable pad are exposed, and such perforations in said second web being positioned for alignment respectively with the opposed perforations in the two external walls of the stoma bag,
    an adhesive coating for attachment of the filter to the stoma bag being provided on that side of said second web remote from such pads and on any part of that side of said first web adjacent to such pads that extend beyond the edge of the second web.

2. A venting device according to claim 1, wherein the portion of each gas-permeable pad exposed to the atmosphere is at least a portion of the edge of the pad.

3. A venting device according to claim 1, which comprises one gas-permeable pad, which is situated toward one end of said first web and positioned so as, in use, to cover one of said opposed perforations, and wherein the other end of the venting device is adapted to seal the other of said opposed perforations in a gas tight manner.

4. A venting device according to claim 1, wherein a single gas-permeable pad extends for the entire length or for a major part of the length of the web and is positioned so as, in use, to cover said opposed perforations.

5. A venting device according to claim 1, which is substantially of elongate waisted shape.

6. A venting device according to claim 5, which is substantially of dumb-bell shape.

7. A venting device according to claim 1, wherein the edge of said first web coincides with the edge of each gas-permeable pad over at least part of each pad and the edge of said second web coincides with the edge of each gas-permeable pad over that part of such pad, and wherein at least a portion of the edge of each gas-permeable pad is exposed.

8. A venting device according to claim 1 wherein substantially all surfaces of each gas-permeable pad adjacent to a web are adhesively secured to that web.

9. A stoma bag comprising first and second opposed walls joined together around their edges, the first wall being provided with an opening to register with a stoma on a patient, the first wall containing toward an upper edge thereof a first perforation and the second wall containing a second perforation opposed to the said first perforation; and carrying a venting device according to claim 1, the venting device being arranged in a folded position over the said upper edge of the bag in such a manner as to cover the said first and second perforations while permitting the venting of gas through at least one of the said first and second perforations, through the venting device and thus into the atmosphere.

10. A venting device for attachment to a fluid-tight stoma bag, which bag comprises first and second opposed walls joined together around their edges, the first wall being provided with an opening to register with a stoma on a patient, the first wall containing toward an upper edge thereof a first perforation and the second wall containing a second perforation opposed to the said first perforation;
    (i) the venting device being capable of attachment in a folded position over the said upper edge of the stoma bag in such a manner as to cover the said first and second perforations while permitting the venting of gas from the bag through at least one of the said first and second perforations, through the venting device and thus into the atmosphere;
    (ii) the venting device comprising
        (a) a first elongate web,
        (b) a gas-permeable pad having two major surfaces and an edge and containing an odour-absorbing substance, and
        (c) a second elongate web;
    (iii) the gas-permeable pad being adhered to each elongate web with one of its major surfaces adjacent to one face of the first elongate web, with its other major surface adjacent to the second elongate web, and with the edge of each web coinciding with the edge of the pad;
    (iv) the seond elongate web containing two perforations through which two portions, respectively, of the major surface of the pad are exposed, the said two perforations being arranged for alignment, in use, with the afore-mentioned first and second perforations in the walls of the bag;
    (v) the face of the second web remote from the pad being provided with an adhesive coating for attachment of the venting device to the stoma bag; and
    (vi) the edge of the gas permeable pad being, in use, exposed to the atmosphere.

11. A venting device accoriding to claim 10, which is substantially of dumb-bell shape.

12. A stoma bag comprising first and second opposed walls joined together around their edges, the first wall being provided with an opening to register with a stoma on a patient, the first wall containing toward an upper edge thereof a first perforation and the second wall containing a second perforation opposed to the said first perforation; and carrying a venting device according to claim 10, the venting device being arranged in a folded position over the said upper edge of the bag in such a manner as to cover the said first and second perforations while permitting the venting of gas through the said first and second perforations, through the venting device and thus into the atmosphere.

* * * * *